(12) United States Patent
Lee et al.

(10) Patent No.: US 9,194,477 B2
(45) Date of Patent: Nov. 24, 2015

(54) WEARING MONITORING DEVICE FOR MOTION GUIDE DEVICE

(71) Applicant: Hiwin Technologies Corp., Taichung (TW)

(72) Inventors: Po Lin Lee, Taichung (TW); Szu Wei Yu, Taichung (TW)

(73) Assignee: Hiwin Technologies Corp., Situn, Taichung (TW)

( * ) Notice: Subject to any disclaimer, the term of this patent is extended or adjusted under 35 U.S.C. 154(b) by 18 days.

(21) Appl. No.: 14/177,262

(22) Filed: Feb. 11, 2014

(65) Prior Publication Data

US 2015/0226311 A1 Aug. 13, 2015

(51) Int. Cl.
*F16H 25/22* (2006.01)
*F16H 57/01* (2012.01)
*G01N 33/28* (2006.01)

(52) U.S. Cl.
CPC ............ *F16H 57/01* (2013.01); *F16H 25/2214* (2013.01); *G01N 33/2858* (2013.01); *F16H 2057/012* (2013.01)

(58) Field of Classification Search
CPC .............................. F16H 25/2214; F16C 29/06
See application file for complete search history.

(56) References Cited

U.S. PATENT DOCUMENTS

| 3,553,672 | A | * | 1/1971 | Smith ........................... 340/627 |
| 4,070,660 | A | * | 1/1978 | Tauber .......................... 340/631 |
| 4,414,863 | A | | 11/1983 | Heino |
| 5,969,903 | A | * | 10/1999 | Parsoneault et al. ........ 360/99.08 |
| 7,299,703 | B2 | | 11/2007 | Balasu et al. |
| 7,523,682 | B2 | | 4/2009 | Liao et al. |
| 2006/0045406 | A1 | | 3/2006 | Iwamoto et al. |
| 2012/0014631 | A1 | * | 1/2012 | Huang et al. ................... 384/446 |

* cited by examiner

*Primary Examiner* — Thomas R. Hannon
(74) *Attorney, Agent, or Firm* — Charles E. Baxley

(57) ABSTRACT

A motion guide device includes a movable member attached onto an elongated member for forming a ball guiding passage and for receiving ball bearing members between the elongated member and the movable member, a detecting device includes a magnetic member and an insulated tube engaged into a hole of the movable member, and a warning device is coupled between the movable member and the magnetic member for generating a warning signal when the movable member and the magnetic member are electrically connected together with worn particles and for allowing the user to examine and to repair the motion guide device or the ball screw device when required.

4 Claims, 5 Drawing Sheets

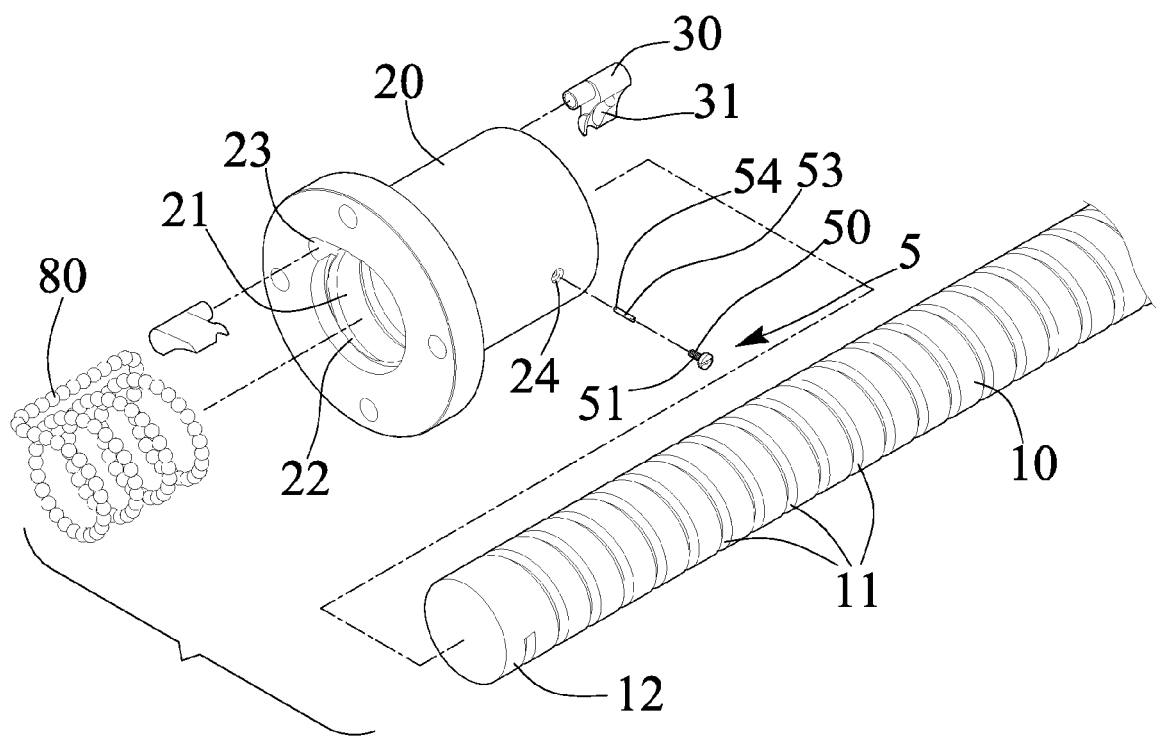
F I G. 1
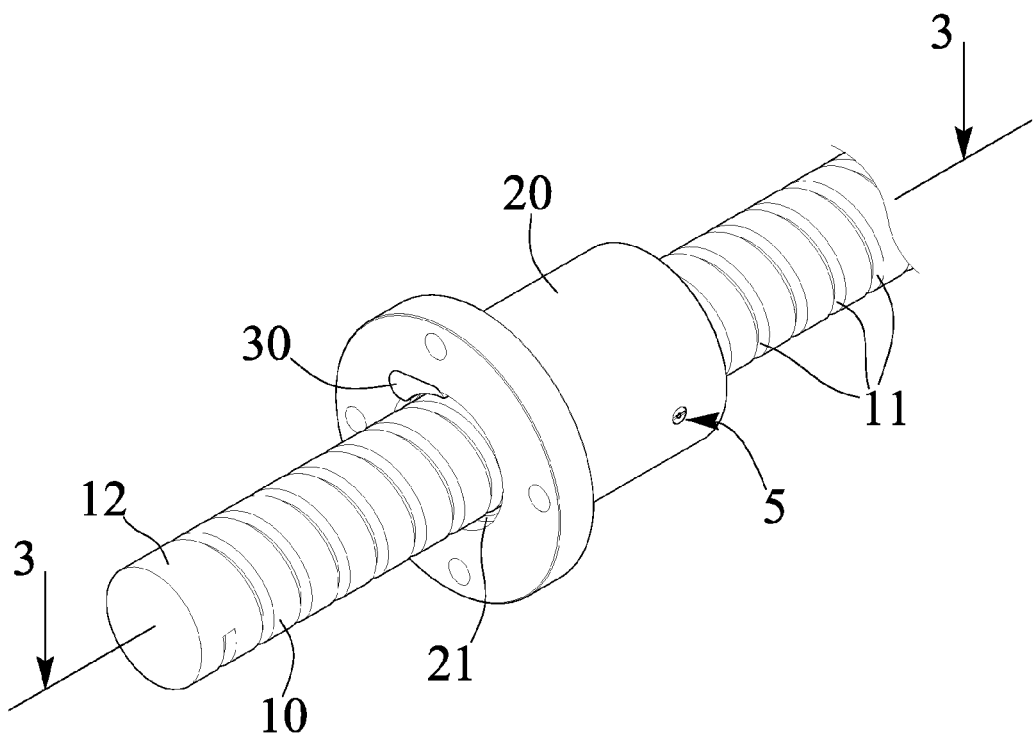
F I G. 2

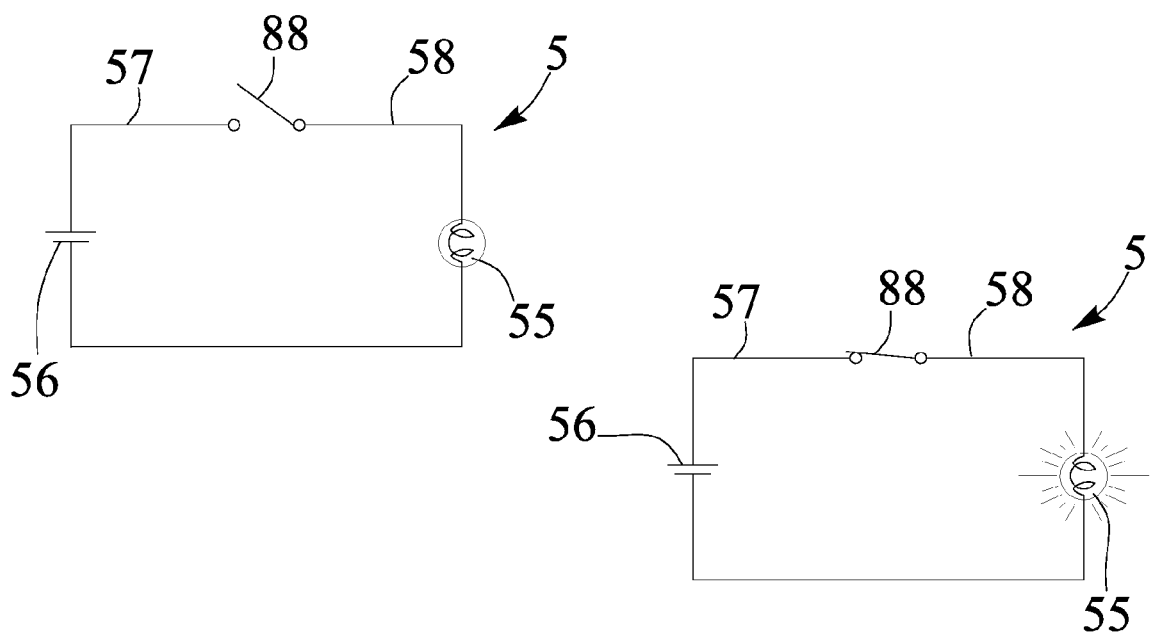
F I G. 6  F I G. 7
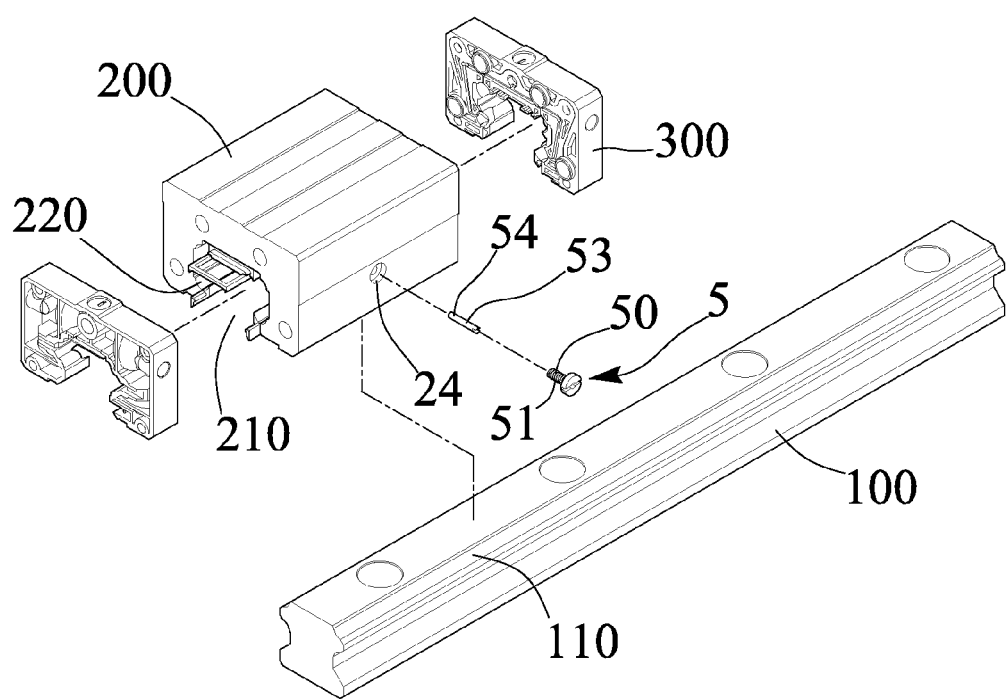
F I G. 8

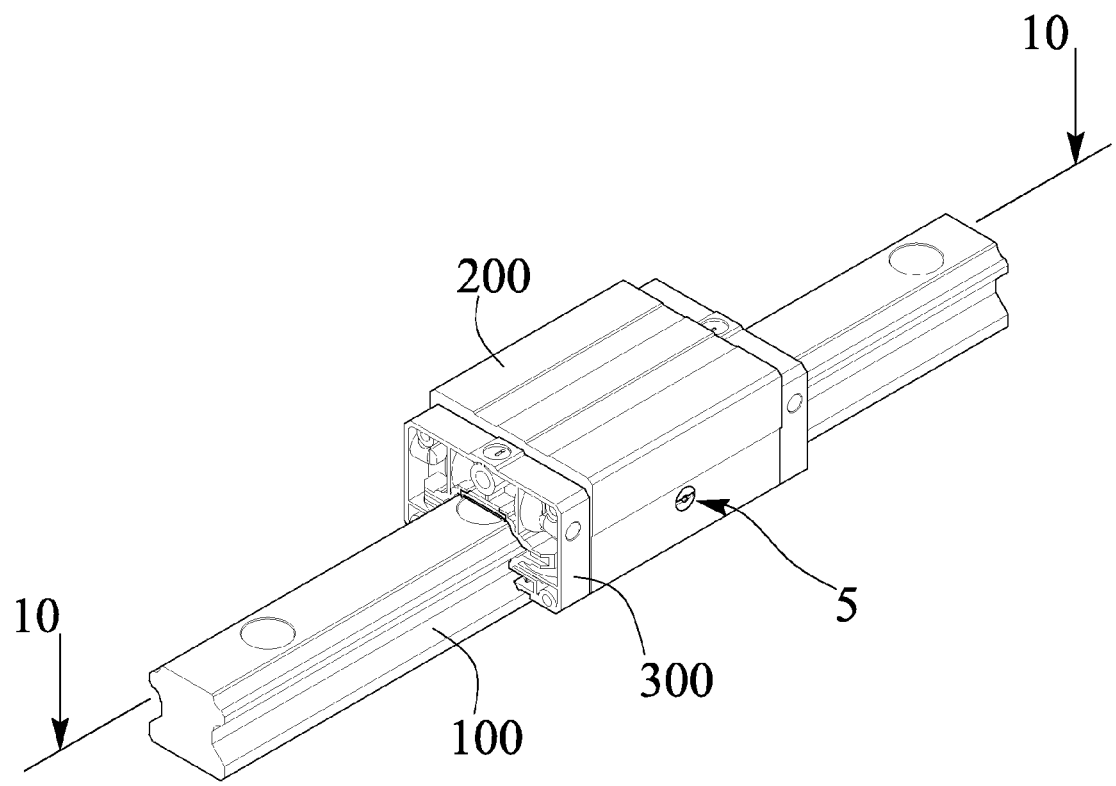
F I G. 9
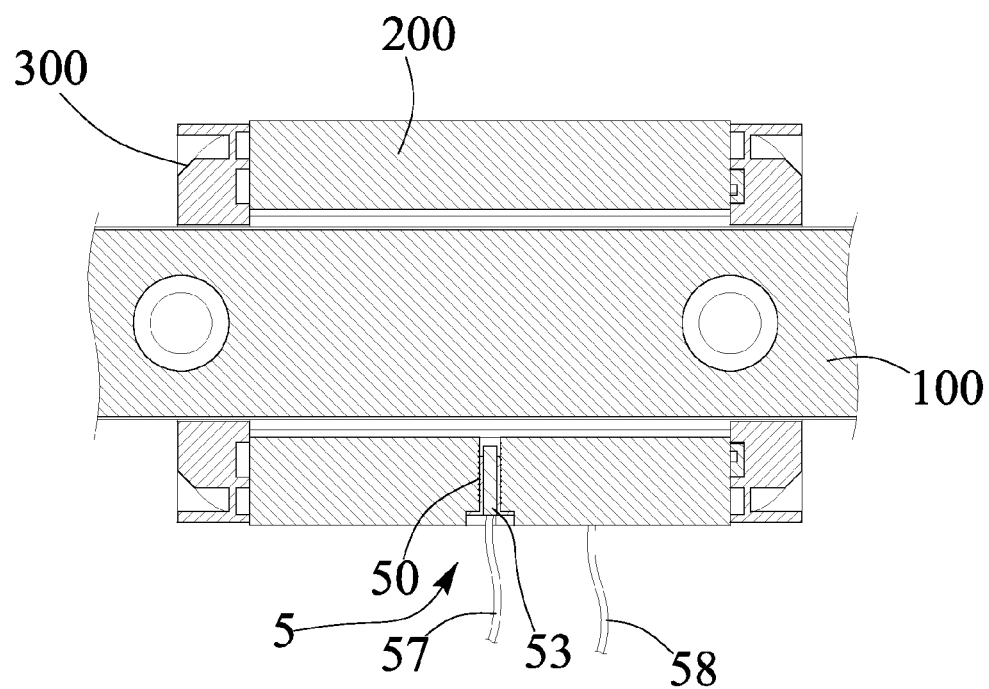
F I G. 10

WEARING MONITORING DEVICE FOR MOTION GUIDE DEVICE

BACKGROUND OF THE INVENTION

1. Field of the Invention

The present invention relates to a ball screw device or a linear motion guide device having a wearing monitoring device, and more particularly to a ball screw device or a linear motion guide device having a wearing monitoring device for sensing or detecting a wearing or failure of the ball bearing members and for generating a warning signal and for allowing the user to examine and to repair the linear motion guide device or the ball screw device when required.

2. Description of the Prior Art

Typical ball screw devices or linear motion guide devices comprise a ball nut or sliding member slidably attached or mounted onto an elongated member or screw shaft, and having one or more elongated or helical ball guiding passages formed therein for forming or defining an endless multiple-turn, helical raceway therein, and a number of ball bearing members engaged in the endless multiple-turn, helical raceway for facilitating the sliding movement between the elongated member or screw shaft and the ball nut or sliding member.

Normally, the elongated member or screw shaft and the ball nut or sliding member may be slid or moved in a great speed relative to each other, and the ball bearing members may have a good chance to become wear or failure after use, and the typical ball screw devices or linear motion guide devices may also become failure after use.

For example, U.S. Pat. No. 7,523,682 to Liao et al. discloses one of the typical linear motion guide devices including an arrangement for smoothly guiding two sliding members to slide relative to each other. However, Liao et al. failed to teach an integrated circuit disposed for detecting a moving frequency between the two sliding members, particularly when the typical linear motion guide devices have become wear or damaged or failure after use.

U.S. Pat. No. 4,414,863 to Heino, and U.S. Pat. No. 7,299,703 to Balasu et al. disclose the other typical bearing balls escape and wear annunciator arrangements for ball screws including an arrangement for detecting a load wearing and including a pair of electrical sensors installed on a load path that is threadedly engaged with the screw shaft, and the electrical sensors are required to be engaged into the helical threaded portions or grooves of the screw shaft in order to detect the load wearing.

However, it will be difficult to install or dispose or attach or mount the electrical sensors into the load path, and the electrical sensors may not be used to suitably or effectively sense or detect the wear or failure of the ball bearing members due to the filling or engagement of the grease or lubricating oil in the endless multiple-turn, helical raceway that receives the ball bearing members.

U.S. Patent Publication No. 2006/0045406 to Iwamoto et al. discloses a further typical linear motion guide device including a detecting device having a magnetic member and an integrated circuit disposed for detecting a moving frequency that communicates with nearby component for the purposes of installing sensors compactly in a bearing assembly while detecting the target component in a stable manner.

Actually, in Iwamoto et al., a sensor-equipped wheel support bearing assembly is disclosed and includes rotation sensors installed in compact in the bearing assembly for detecting, in a stable fashion, the number of revolutions of the vehicle wheel and the load acting on the vehicle wheel.

However, in Iwamoto et al., the rotation sensors are installed in the bearing assembly for detecting the number of revolutions of the vehicle wheel and the load acting on the vehicle wheel, and a number of displacement sensor assemblies are further required and disposed at respective locations circumferentially equidistantly spaced from each other, and the rotation sensor is positioned between the displacement sensors for detecting the number of revolutions of the vehicle wheel and the load acting on the vehicle wheel, but may not be used for detecting whether the typical linear motion guide device has become failure or not.

The present invention has arisen to mitigate and/or obviate the afore-described disadvantages of the conventional wearing monitoring devices for ball screw devices or linear motion guide devices.

SUMMARY OF THE INVENTION

The primary objective of the present invention is to provide a ball screw device or a linear motion guide device including a wearing monitoring device for easily and readily sensing or detecting a wear or failure of the ball bearing members and for generating a warning signal and for allowing the user to examine and to repair the linear motion guide device or the ball screw device when required.

In accordance with one aspect of the invention, there is provided a motion guide device comprising an elongated member including a groove formed on an outer peripheral surface thereof, a movable member including a bore formed therein for receiving the elongated member and for movably attaching onto the elongated member, and including a groove formed therein and aligned with the groove of the elongated member for forming a ball guiding passage between the elongated member and the movable member, and the movable member including a hole formed therein, a number of ball bearing members disposed in the ball guiding passage that is formed between the elongated member and the movable member for facilitating a sliding movement between the elongated member and the movable member, a detecting device including a magnetic member engaged into the hole of the movable member, and an insulated tube engaged into the hole of the movable member and engaged between the movable member and the magnetic member for spacing the movable member and the magnetic member from each other, and a warning device coupled between the movable member and the magnetic member for selectively generating a warning signal when the movable member and the magnetic member are selectively and electrically connected together with the worn particles or the like.

The hole of the movable member is a screw hole, and the insulated tube includes an outer thread engaged with the screw hole of the movable member for detachably mounting the insulated tube of the detecting device to the movable member.

The magnetic member includes an inner end flush with the insulated tube. The detecting device includes a power supply coupled to the warning device for energizing the warning device and the like. The magnetic member is selected from a permanent magnetic member.

Further objectives and advantages of the present invention will become apparent from a careful reading of the detailed description provided hereinbelow, with appropriate reference to the accompanying drawings.

BRIEF DESCRIPTION OF THE DRAWINGS

FIG. 1 is a partial exploded view of a ball screw device including a wearing monitoring device in accordance with the present invention;

FIG. 2 is a partial perspective view of the ball screw device for attaching or mounting the wearing monitoring device;

FIG. 6 is a plan schematic view illustrating the electric circuit of the wearing monitoring device of the ball screw device;

FIG. 7 is another plan schematic view similar to FIG. 6, illustrating the operation of the wearing monitoring device of the ball screw device;

FIG. 8 is a partial exploded view illustrating a wearing monitoring device for the linear motion guide device;

FIG. 9 is a perspective view of the linear motion guide device as shown in FIG. 8;

FIG. 10 is a partial cross sectional view of the linear motion guide device, taken along lines 10-10 of FIG. 9.

DETAILED DESCRIPTION OF THE PREFERRED EMBODIMENT

Figure 3:
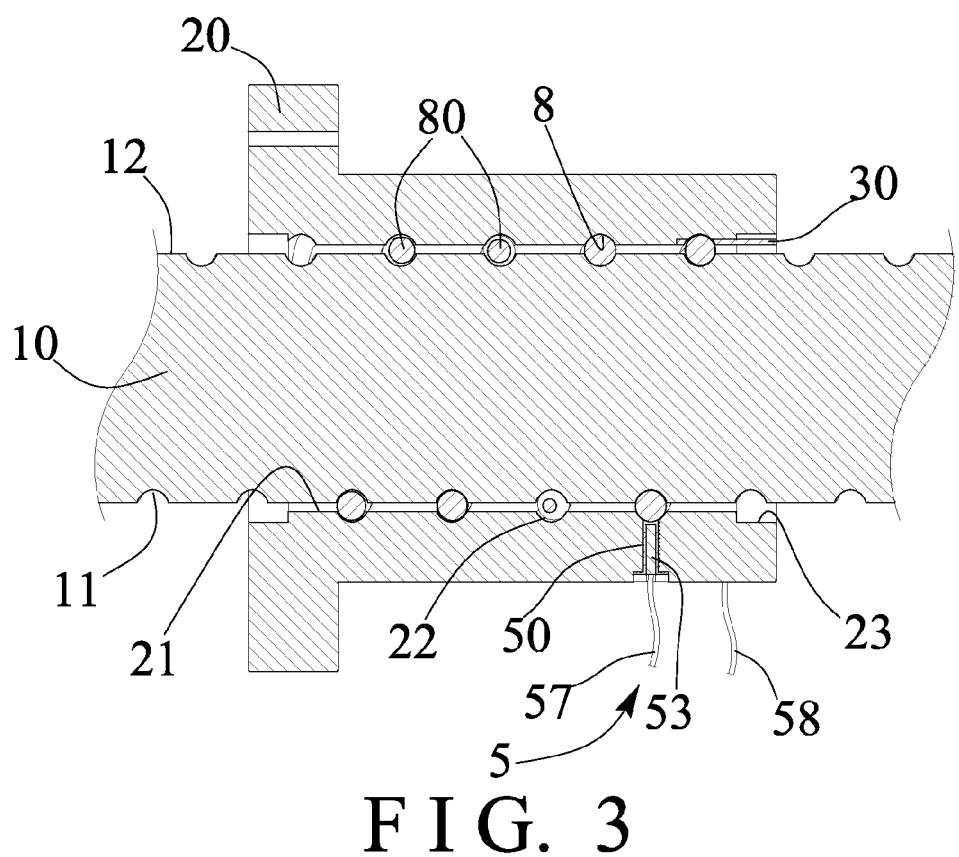
FIG. 3 is a partial cross sectional view of the ball screw device, taken along lines 3-3 of FIG. 2.

Referring to the drawings, and initially to FIGS. 1-3, a linear motion guide device or a ball screw device in accordance with the present invention comprises an elongated bolt or screw shaft or member 10 including a helical threaded portion or groove 11 formed on the outer peripheral portion or in the outer peripheral surface 12 thereof, and a movable member 20, such as a ball nut 20 including a screw hole or bore 21 formed therein for engaging with the elongated member 10 and for movably attaching onto the elongated member 10, and the bore 21 of the ball nut 20 is formed or defined by a helical threaded portion or groove 22 which is formed in the inner peripheral portion of the ball nut 20.

The helical threaded groove 11 of the member 10 is aligned with the helical threaded groove 22 of the ball nut 20 for forming or defining a ball guiding passage 8 between the elongated member 10 and the ball nut 20, and the ball nut 20 includes one or more depressions 23 formed therein and communicated with the helical threaded groove 22 or the ball guiding passage 8 of the ball nut 20 for engaging with deflecting devices 30 which are attached to the depressions 23 of the ball nut 20 and each of which includes a deflecting pathway 31 formed therein (FIG. 1) and aligned with or communicating with the ball guiding passage 8 of the ball nut 20 for forming or defining a single endless multiple-turn, helical raceway 8 and for slidably receiving a number of ball bearing members 80 and for facilitating the sliding or rotational movement between the elongated member 10 and the movable member or ball nut 20.

The ball nut 20 further includes a screw hole 24 formed therein and preferably, but not necessarily communicating with the groove 22 of the movable member or ball nut 20 for engaging with a detecting device 5. For example, the detecting device 5 includes an insulated tube 50 having an outer thread 51 (FIGS. 1, 4-5) for engaging with the screw hole 24 of the ball nut 20 and thus for detachably securing the insulated tube 50 of the detecting device 5 to the ball nut 20, and the insulated tube 50 includes a bore or orifice 52 formed therein for engaging with a core or magnetic member 53. It is preferable, but not necessary that the magnetic member 53 is flush with the insulated tube 50 (FIGS. 4-5).

Figure 4:
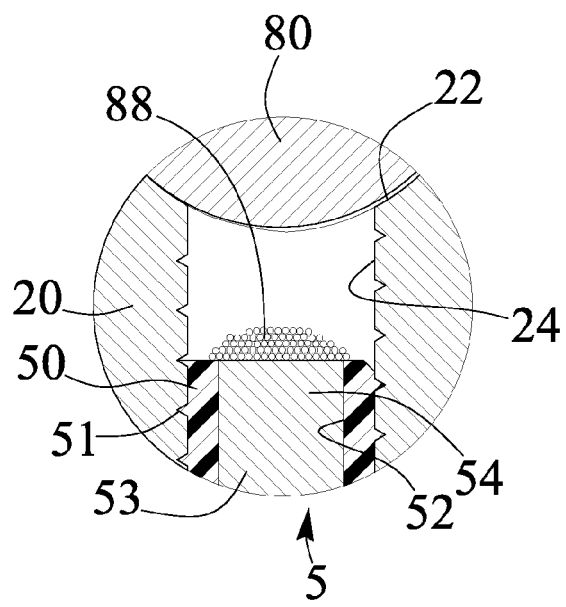
FIGS. 4, 5 are enlarged partial cross sectional views illustrating the operation of the wearing monitoring device of the ball screw device.
Figure 5:
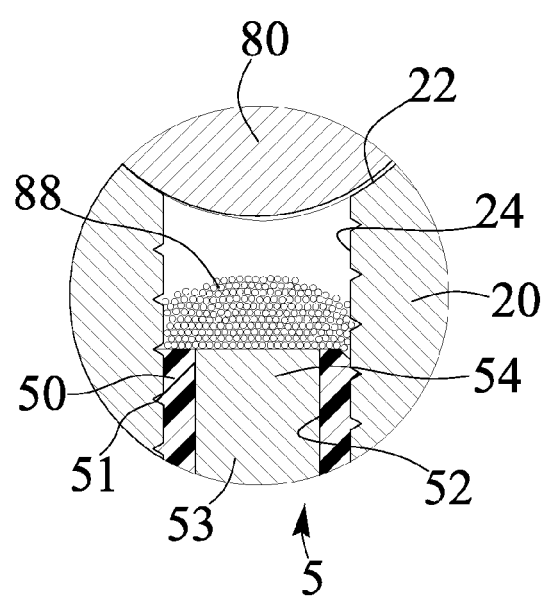

As best shown in FIGS. 4 and 5, the magnetic member 53 includes an inner end 54 directed toward the ball bearing members 80, but spaced from the ball bearing members 80, and the magnetic member 53 is spaced from the ball nut 20 with the insulated tube 50; i.e., the magnetic member 53 is not electrically connected to the ball nut 20 and the ball bearing members 80. As shown in FIG. 6, a warning device 55 is coupled to the battery or power supply 56 and may be selected from a buzzer or light member 55 for generating a warning signal, such as a warning sound or a warning light, the magnetic member 53 and the ball nut 20 are electrically connected to the power supply 56 and the warning device 55 with wires or cables 57, 58 respectively (FIG. 3). The magnetic member 53 may be selected from a permanent magnetic member 53 or an electrico-magnetic member 53.

In operation, as shown in FIG. 3, the movement of the ball bearing members 80 through the endless multiple-turn, helical raceway 8 of the ball screw device, and/or the movement of the ball nut 20 relative to the elongated member 10 may generate worn chips or particles 88 or the like (FIGS. 4, 5), and the worn chips or particles 88 may be attracted to the inner end 54 of the magnetic member 53, and when the worn chips or particles 88 are not great enough to be contacted or engaged with the ball nut 20, the magnetic member 53 and the ball nut 20 and/or the cables 57, 58 are separated from each other and are not electrically connected together, such that the electric circuit between the power supply 56 and the warning device 55 is opened (FIG. 6) and such that the warning device 55 will not be energized with the power supply 56 at this moment.

As shown in FIG. 5, when the worn chips or particles 88 are great enough to be contacted or engaged with the ball nut 20, the magnetic member 53 and the ball nut 20 and/or the cables 57, 58 will be electrically coupled together with the cables 57, 58 and the worn chips or particles 88, and at this moment, the warning device 55 may be energized with the power supply 56 (FIG. 7) in order to generate a warning signal, such as a warning sound or a warning light, and thus for allowing the user to examine and to repair the ball screw device when the warning signal is generated.

Alternatively, as shown in FIGS. 8-10, illustrated is a linear motion guide device comprising an elongated member 100 including one or more longitudinal grooves 110 formed on the outer peripheral portion or surface thereof, and a movable member 200, such as a block 200 including a bore 210 formed therein for engaging with the elongated member 100 and for movably attaching onto the elongated member 100, and the bore 210 of the movable member 200 is formed by one or more longitudinal grooves 220 which are formed in the inner peripheral surface or portion of the movable member 200, and the movable member 200 also includes a screw hole 24 formed therein.

Figure 11:
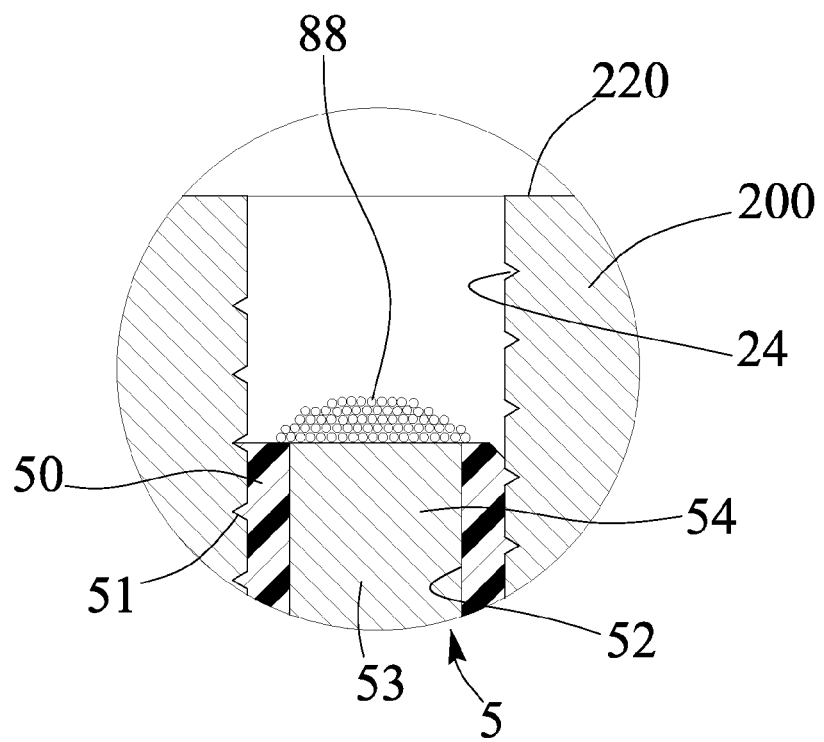
FIGS. 11, 12 are enlarged partial cross sectional views illustrating the operation of the wearing monitoring device of the linear motion guide device.
Figure 12:
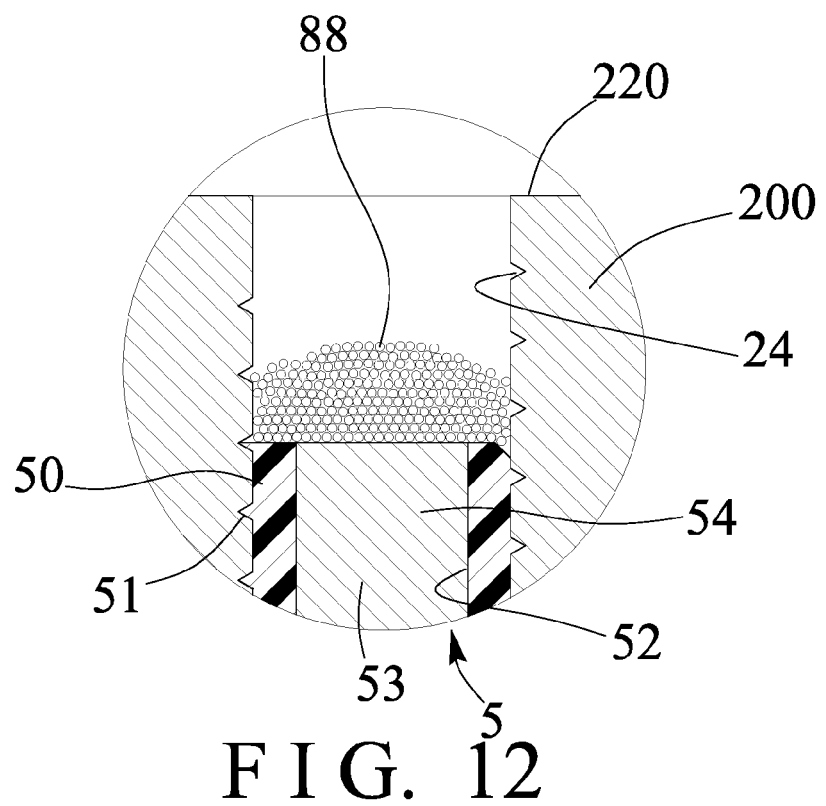

It is preferable, but not necessary that the screw hole 24 of the movable member 200 is communicating with the groove 220 of the movable member 200 for engaging with the detecting device 5. For example, the detecting device 5 also includes an insulated tube 50 having an outer thread 51 (FIGS. 11-12) for engaging with the screw hole 24 of the movable member 200 and thus for detachably securing the insulated tube 50 of the detecting device 5 to the movable member 200, and the insulated tube 50 includes an orifice 52 formed therein for engaging with a core or magnetic member 53. The magnetic member 53 and the movable member 200 may be electrically connected together with the cables 57, 58 and the worn chips or particles 88.

Accordingly, the ball screw device or a linear motion guide device in accordance with the present invention includes a wearing or worn out monitoring device for easily and readily sensing or detecting a wear or failure of the ball bearing members and for generating a warning signal and for allowing the user to examine and to repair the linear motion guide device or the ball screw device when required.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

We claim:

1. A motion guide device comprising:
   an elongated member including a groove formed on an outer peripheral surface thereof,
   a movable member including a bore formed therein for receiving said elongated member and for movably attaching onto said elongated member, and said movable member including a groove formed therein and aligned with said groove of said elongated member for forming a ball guiding passage between said elongated member and said movable member, and said movable member including a hole formed therein, said hole of said movable member being a screw hole,
   a plurality of ball bearing members disposed in said ball guiding passage that is formed between said elongated member and said movable member for facilitating a sliding movement between said elongated member and said movable member,
   a detecting device including a magnetic member engaged into said screw hole of said movable member, and an insulated tube engaged into said screw hole of said movable member and engaged between said movable member and said magnetic member for spacing said movable member and said magnetic member from each other, said insulated tube including an outer thread engaged with said screw hole of said movable member for detachably mounting said insulated tube of said detecting device to said movable member, and
   a warning device coupled between said movable member and said magnetic member for selectively generating a warning signal when said movable member and said magnetic member are selectively and electrically connected together with worn particles.

2. The motion guide device as claimed in claim 1, wherein said magnetic member is selected from a permanent magnetic member.

3. The motion guide device as claimed in claim 1, wherein said magnetic member includes an inner end flush with said insulated tube.

4. The motion guide device as claimed in claim 1, wherein said detecting device includes a power supply coupled to said warning device.

\* \* \* \* \*